Jan. 1, 1974 M. OWNBEY Plant Pat. 3,419
DICENTRA PLANT
Filed Aug. 23, 1971
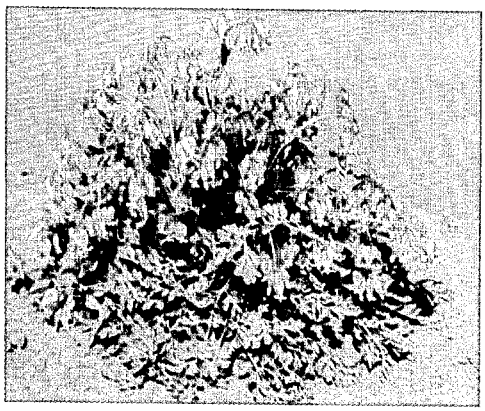
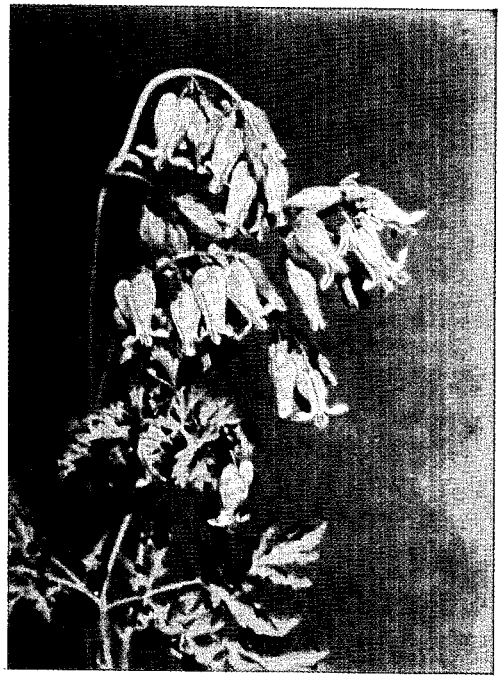
Inventor,
Marion Ownbey,
by John H. Lamoree,
his Attorney.

United States Patent Office

Plant Pat. 3,419
Patented Jan. 1, 1974

3,419
DICENTRA PLANT

Marion Ownbey, Pullman, Wash., assignor to The Wayside Gardens Company, Mentor, Ohio Filed Aug. 23, 1971, Ser. No. 174,066
Int. Cl. A01h 5/00
U.S. Cl. Plt.—68 1 Claim This application is directed to a new and distinct variety of Dicentra plant.

The present new variety was first developed by me in Pullman, Wash., and there asexually reproduced by me by root division.

The new variety was developed by an intentional cross pollination made by the transfer of pollen from the staminate parent *Dicentra peregrina,* a wild species from Japan, to the seed or pistillate parent Dicentra "Paramount," U.S. Plant Pat. No. 1,594.

Dicentra Paramount is a selection from an open pollinated presumed $F_3$ population derived from a *Dicentra formosa* ssp. *oregana*×*Dicentra eximia* cross.

Seeds from the controlled cross pollination were planted and the new variety was selected from the resulting seedlings.

The new variety is illustrated in the drawing which shows in the upper view the present variety of Dicentra plant in bloom, and in the lower view an enlargement of one of the typical flower stalks, with flowers and leaves, of the plant in the upper view.

The color references herein are to the Royal Horticultural Society Colour (1941).

The plant is generally similar to the Dicentra "Paramount," except for the shape, color, abundance, sterility and lasting quality of the flowers. Unlike the Dicentra "Paramount," its flowers or bangles are more truly heart-shaped, and have strongly recurved outer petals which are generally bright Rose Red, RHS 724/3, but may range from RHS 025 to 025/1, in color with narrow white margins on the petals. In the illustration the colors are less blued than in the actual plant. Its panicles are looser and bear a dozen or more sterile flowers which individually last several weeks. It has a truly ever-blooming habit, a single well grown plant producing as many as fifty to one hundred flower clusters from spring to fall in a single season.

ROOTS

The root of the plant is usual, being a fibrous mass, short rhizomatous, the rhizomes being vertically disposed. The root is of medium size, shallowness, and lateral spread.

The roots also have disease, drought, winter resistance, protected and unprotected, usual for Dicentra plants. They have withstood temperatures below zero F. without snow cover and as low as minus 30° F. with snow cover.

The roots thrive in both acid and neutral soils, well drained, but sand or sandy loam are preferred.

EXPOSED STRUCTURE OF THE PLANT

The plant is a hardy, herbaceous, perennial. It grows generally upright and is dense and compact and clumped, with a rounded peak. A two year old plant averages about ten inches high, and eighteen inches across, not including over-topping flower stalks or peduncles, which bring the total height in flowering plant to from fifteen to eighteen inches.

The general shape is that of a rounded mound. The plant is of vigorous growth and resistant to low temperatures both when protected and unprotected. It appears to be relatively free from diseases and has good resistance to drougth and wet seasons. It is exceptionally resistant to the usual insect pests.

PREFERRED CONDITIONS OF GROWTH

The plant thrives best, both as to growth and flowering, in the full sun, but it tolerates medium to dense shade. The particular exposure is not critical, but a well drained, fertile, sand or sandy loam soil is preferred for best growth and bloom.

THE PARTS OF THE EXPOSED PLANT

The flower stalks are generally upright and curving, and drooping at their ends. They are slightly branched. Generally they are adequate to support the foliage and blooms well.

The color of both the old and new foliage is blue-green, comparable to Chrysocolla green, RHS 56/3. It is generally uniform both on the old and new growth.

The length of the flower stalks is from about fifteen to eighteen inches on the average. The stalks are smooth and naked in texture, and are grouped and divergent in arrangement. The branching is sparse and alternate, with smooth and naked branches colored blue-green. The branches are relatively short and flexible, but adequate to support the bloom and foliage well.

THE FOLIAGE

The foliage generally is compact with the leaves alternate and basal. The leaves are abundant in quantity. Both the old and new leaves are a blue-green, RHS 56/3, on the top and bottom. The color is generally uniform. The leaf blades are of average medium size, reaching a maximum length of about six inches and a minimum length of three inches. The maximum width is six inches and minimum width of three inches. The leaf blades are generally twice ternate, then pinnately divided, the general outline being deltoid, as usual in this group of Dicentras. The margins of the tertiary divisions are again deeply divided, the bases of the tertiary divisions being cuneate. The apices of the ultimate divisions are mucronate. Both the upper and lower faces are glabrous and glaucous, more glaucous than is usual. Their persistency on the plant is excellent.

The leaf steams are smooth and naked, blue-green comparable to the leaf color, and about eight inches in length. They are strong.

For the best quality of blooms, the variety prefers cool temperature areas in a sunny exposure, but tolerates shade. It blooms well in northern and southern exposures, but best in eastern and western exposures. It blooms best in moderately moist, cool, seasons in a well drained moist rich sandy loam soil, either acid or neutral, but also blooms well in rocky soil.

The quantity of blooms generally is increased by increased sunlight and fertility, and adequate, but not excessive, water. The color is intensified by full sunlight and cooler temperatures. While more flowers are produced in the full sunlight, they fade more quickly. At higher temperatures and with increasing shade the color fades. The plant tends to become dormant in hot, dry weather. Ordinarily the conditions of sun, shade, moisture have little effect on the size of the bloom.

BLOOMING PERIOD

The plant blooms generally from late April through October, with a few flowers at first and reaching a peak in quantity in June, or sometimes in September. Generally it blooms continuously throughout the blooming period, but sometimes blooms recurrently.

The buds generally are medium large, and are truly heart shaped with smooth glossy aspect. They are supported in the usual drooping or pendant position on lateral branches.

The color when the sepals first divide is unusual, being a Rose Red, comparable to RHS 724, and this color is retained when the sepals first divide, as the petals begin to unfurl, and when half blown.

The sepals generally are inconspicuous and small, as is usual for Dicentra plants. The calyx is of the usual shape and small and inconspicuous.

The peduncles average from fifteen to eighteen inches, overtopping the leaves and have the usual surface texture. Their color is blue-green, comparable to the leaf color. They are very strong. The pedicels average from one half to one inch and have the usual surface texture. They are blue-green or somewhat reddish in color with the small red bracts at the base. They are of average strength.

THE BLOOM

The bloom ranges from one half inch to five eighths of an inch in average diameter. Several hundred are borne on a plant. The blooms are borne in panicles, and on the growing plant last from about two to four weeks, depending upon the weather. When cut, they last from one to two weeks, but sometimes longer.

The petalage is usual, there being four petals, two of which are large and two of which are small. They are arranged in two whorls. Their color overall is Rose Red, comparable to RHS 724/3 when the plant is growing under preferred conditions in the sun. Under other less desirable conditions, the color approaches Rose Madder, RHS 23/1. The color tends to be lighter on plants growing in the shade or under undesirable conditions. The flower is Rose Red at the center and White at the inner petals. The outer petals are Rose Red with narrow white edges at the tips. The bases of the petals also are Rose Red. The insides of the petals are Rose Red and white. The reverses are Rose Red.

The general tonality of the blooming plant from a distance is a Rose Red. The red coloring in all cases becomes less intense with less favorable conditions of temperatures, soil, and shade. The old flowers become paler after two or three weeks, then gradually wither and drop off.

The petal texture is smooth and glabrous, as usual. The outer petals are large, strongly saccate, with large and very unusual strongly recurved tips. The inner petals are smaller and elongated, and are hooded and crested at the apex. They have the usual arrangement for Dicentra plants. They are free from petaloids in the center, until the fall of the entire flower.

An unusual feature of the flowers is that they are more truly heart-shaped, as shown clearly in the lower view in the drawing. They are of exquisite quality and have a faint fragrance.

Generally, the stamens are usual for Dicentra plants, except that they are pollen abortive. They are of the usual yellow color with white filaments and yellow pollen. The styles and stigma are usual in size and shape and reddish in color.

The flower has a single ovary. The fruit is abortive. If developed at all, it is usually empty, or contains not more than a single seed. This is quite unusual for these plants.

The variety apparently can be grown satisfactorily over much of the northern United States and places of similar climate.

The variety combines the most desirable characteristics of three wild species of Dicentra, one from eastern North America, one from western North America, and one from Asia. Its triploid chromosome complement includes one set of chromosomes from each *Dicentra formosa* ssp. *oregana* (Eastwood) Munz, *Dicentra eximia* (KER) Torrey, and *Dicentra peregrina* (Rudolph) Makino. This tri-specific parentage gives it great adaptability and hybrid vigor, and the resulting partial triploid sterility gives it a greater potential for continuous blooming than possessed by any previously introduced cultivar. Because of its Asiatic parentage, its flowers are larger and more truly heart shaped, as in the well known *Dicentra spectabilis,* and are clearer in color than those of any previous Dicentra plant.

The main distinguishing characteristics of this variety are its spring to fall profusion of large, long lasting, more truly heart-shaped flowers, their clear Rose Red, and their long recurved tips on the outer petals; its striking blue-green leaves; and its hybrid vigor.

Having thus described by invention I claim:

1. The new and distinct variety of Dicentra plant herein shown and described.

No references cited.

ROBERT E. BAGWILL, Primary Examiner